United States Patent [19]

Lagana'

[11] Patent Number: 5,399,755
[45] Date of Patent: Mar. 21, 1995

[54] PROCESS AND EQUIPMENT FOR THE HYDROLYSIS OF RESIDUAL UREA IN THE WATER FROM SYNTHESIS PLANTS

[75] Inventor: Vincenzo Lagana', Milan, Italy

[73] Assignee: Urea Casale S.A., Lugano, Switzerland

[21] Appl. No.: 965,741

[22] Filed: Oct. 23, 1992

[30] Foreign Application Priority Data

Oct. 23, 1991 [CH] Switzerland ............ 3087/91

[51] Int. Cl.⁶ ............................. C07C 273/14
[52] U.S. Cl. ....................... 564/63; 210/750; 210/752; 423/358; 564/32
[58] Field of Search ............. 564/69, 73, 32; 423/358; 210/750, 752

[56] References Cited

U.S. PATENT DOCUMENTS

| | | | |
|---|---|---|---|
| 4,341,640 | 7/1982 | Landis | 210/752 |
| 4,456,535 | 7/1984 | Zuidam et al. | 210/750 |
| 4,552,979 | 11/1985 | Stokes | 564/69 |
| 5,223,238 | 6/1993 | Czuppon | 423/359 |

FOREIGN PATENT DOCUMENTS

0059516 9/1982 European Pat. Off. .

*Primary Examiner*—Glennon H. Hollrah
*Assistant Examiner*—Brian M. Burn
*Attorney, Agent, or Firm*—Ostrolenk, Faber, Gerb & Soffen

[57] ABSTRACT

Process for the hydrolysis of urea contained in the process water from plants for the synthesis of urea consisting of the thermic treatment of the water containing urea and of the removal by stripping of the compounds from decomposition of the urea ($CO_2$ and $NH_3$) in a series of stages in series with superimposed flow.

The equipment is a vertical column with superimposed modules with weirs which penetrate in two successive modules and give the solution a rising movement.

9 Claims, 1 Drawing Sheet

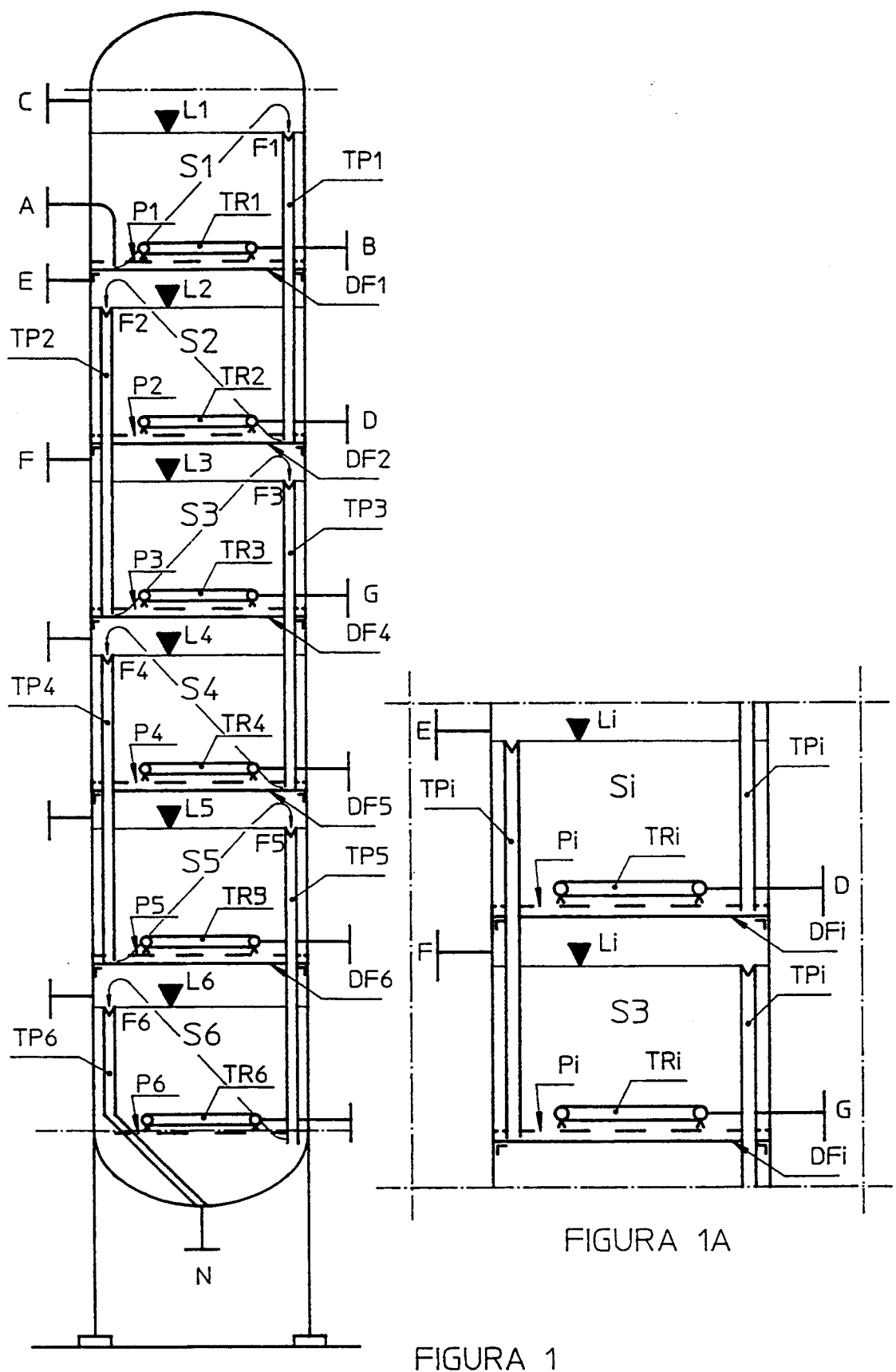
FIGURA 1
FIGURA 1A

PROCESS AND EQUIPMENT FOR THE HYDROLYSIS OF RESIDUAL UREA IN THE WATER FROM SYNTHESIS PLANTS

BACKGROUND OF THE INVENTION

This invention concerns a process for the hydrolysis of urea contained in process water from the synthesis of urea via the reaction of ammonia and carbon dioxide, and containing amounts of urea varying between 100 and 30,000 ppm and for the possible contemporaneous elimination of residual $NH_3$ and $CO_2$.

This invention also includes equipment for carrying out said process, comprising at least a container enclosed in a shell, an inlet for the water containing residual urea, an inlet for the steam, an inlet for the stripping gas and/or modify the solution pH.

The synthesis of urea is based on reaction of ammonia and of CO2 in order to produce ammonium carbamate, which through high temperature dehydration produces urea according to the following exothermic reaction scheme:

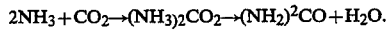

The reaction produces one $H_2O$ mole for each mole of urea, equal to 300 kilos of water for a ton of synthesized urea.

Besides this synthetic water, the plant discharges all the water entering as steam for the final concentration of urea in vacuum groups; it can thus be estimated that the amount of water evacuated from a urea plant is at 470–550 kg/t of urea produced.

The water evacuated from a urea plant contains not only urea but also ammonia and $CO_2$ already present before hydrolysis of the urea, which takes place according to the following endothermic reaction scheme:

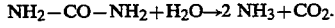

Hydrolysis of the urea must therefore be carried out with a process and in the kind of equipment capable of continuously separating the hydrolysis products ($NH_3$ and $CO_2$), to move the reaction towards the right.

The water contaminated by $NH_3$, $CO_2$, and urea coming from the urea synthesis plant must be treated beforehand according to known technique to separate the existing ammonia and $CO_2$ so as to assist the hydrolysis reaction, and the hydrolysis equipment must be planned in such a way as to separate by stripping the products of decomposition as they are produced according to the reaction schematized above.

The ammonia and the $CO_2$, being the components for the synthesis of urea, are recovered from the hydrolysis reaction through known technique.

Current provisions for the protection of the environment forbid the discharge of water coming from urea plants to avoid the grave problem of eutrophy.

SUMMARY OF THE INVENTION

The main purpose of this invention is to provide a particularly efficient procedure in the scrubbing of refluent water from the synthesis of urea, so as to reduce to a great extent the urea and gas contents in said water, making it uncontaminating and reusable.

The process according to the invention is characterized by the fact that the hydrolysis is carried out in at least four cascade stages of only thermal decomposition at a temperature of between 150° C. and 262° C. and pressure between 15 and 50 bar until the residual contents of urea in the water leaving the last stage is reduced to less than 1 ppm.

Another purpose of the invention is to provide a simple type of equipment for carrying out the process in question, said equipment being characterized by the fact that said shell is a vertical column divided into superimposed modules, each module comprising a bottom wall or baffle (Pi), waterproof and gasproof; a plate (Pi) for the distribution of refluent water situated a few centimeters above said baffle (TRi); a distributor (TRi) of the steam with or without additional stripping gas; and a weir determining the overflow level of an upper module which runs through the entire length of the following lower module thus creating the falling in cascade of the liquid from said upper module to the lower one.

SHORT DESCRIPTION OF THE DRAWING

The various aspects and advantages of the invention will appear more clearly from the description of a particular embodiment shown in the appended drawing in which FIG. 1 is a schematic front view partially in cross-section with a vertical plane of the equipment according to the invention, FIG. 1A being a representation on an enlarged scale of two successive intermediate modules.

DETAILED DESCRIPTION OF THE INVENTION

Advantageously the hydrolyzer according to the invention is vertical, formed by superimposed modules permitting the stripping and removal of reaction products as they form.

REFERRING TO THE DRAWING

The water to be treated suitably preheated enters the first stage of hydrolysis (S1) through inlet A and is evenly distributed along the entire section of the reactor by means of the plate (P1) situated a few centimeters above the baffle (DF1).

The steam enters through inlet B and supplies the necessary heat for hydrolysis while at the same time it strips the products of decomposition leaving from outlet C together with part of the uncondensed steam.

When the liquid reaches level L1 of the weir TP1 it falls into the stage underneath where it is redistributed by plate P2, while the heating and stripping steam enters through inlet D and when the liquid has reached level L2 of weir TP2 it falls into the stage underneath S3 while the products of decomposition leave through outlet E. The liquid runs through each module Si upwardly, for example from left to right in odd modules and from right to left in even modules, as indicated by arrows F1, F2 . . . F6 in FIG. 1.

The same operation is carried out in the successive stages S4, S5, S6 . . . Sn and from this last from weir TPn, in this case TP6, the depurated water with the desired residual urea content leaves through outlet N. The steam entering each stage is distributed by toroid distributor TRi.

According to an additional aspect of the invention, when it is wished to strip with inerts or to add $CO_2$ to the various stages (for example to correct the pH), this injection is effected through the same inlets as the steam (B, D, G) and distributed with toroid TRi.

Operating conditions are as follows:
  1) Feed water to the hydrolyzer:

NH$_3$: 1∓3% weight
CO$_2$: 0.5∓1% weight
urea+biuret: 0.2∓2% weight
H$_2$O: at 100% weight
2) Operating conditions of hydrolyzer:
t=197° C.∓249° C.
p=15 ata∓40 ata
3) Products leaving the hydrolyzer:
NH$_3$: <1 ppm by weight
CO$_2$: <indeterminable quantity
urea: <1 ppm by weight
H$_2$O: about 100%

Preferably the hydrolyzer reaction subject of this invention is substantially a vertical cylinder in stages of decomposition and stripping in successive series in which feeding is carried out at the head and the product (purified water) is extracted from the bottom as shown in FIG. 1.

The products of decomposition and the steam are removed from the head of each stage as soon as they are produced.

The number of stages in the hydrolyzer depends on the degree on purification, that is, of the urea content desired in the water discharged from the hydrolyzer, the contact being capable of varying between 3 and 20%.

To improve hydrolysis and facilitate ammonia stripping, an injection of CO$_2$ can be used at each stage also with the purpose of modifying the pH of the water solution thus favouring the hydrolysis process.

There are various known techniques for hydrolysis which we list below:
1- biological oxidizing
2- treatment with hypochlorite, nitrite
3- enzyme treatment with ureasis
4- reverse osmosis with membranes
5- treatment on exchange resin
6- treatment with phosphoric acid
7- thermic hydrolysis.

As already mentioned, the purpose of this invention is also to provide equipment in which the water from the urea plant is treated thermally while at the same time the products of decomposition (NH$_3$ and CO$_2$) are stripped.

The hydrolysis reactor consists of a column divided into various superimposed modules in series operating as previously described.

The number of modules varies according to the amount of urea contained in the feed water since the urea content after hydrolysis must not be more than 1 ppm in weight; therefore, the greater the urea content in the water to be treated, the greater must be the number of stages and this means a longer residence time of the water in the hydrolyzer.

This residence time, on the basis of the urea content generally found in industrial plants, varies between 10 minutes and 70 minutes.

The water treated in the equipment which is the subject of this invention is sent to a successive stripping column for the elimination of residual ammonia according to known technique.

The advantage of this equipment is that it permits the elimination of a great part of the ammonia by means of steam stripping or gas stripping (air, CO$_2$, inerts, etc.) thus reducing the load in the above-mentioned successive stage for stripping ammonia.

EXAMPLE

An industrial plant for the production of 1750 tons/day of urea produces 36,000 kg/h of process water which after a first stripping stage of part of the ammonia and of the CO$_2$ is fed to the hydrolyzer, of this invention.

Composition of the feed:

| | |
|---|---|
| NH$_3$ | 1.5% weight |
| CO$_2$ | 0.8% weight |
| urea | 0.1% weight |
| H$_2$O | 97.6% weight |
| | 100.0% weight |

After thermal treatment in the hydrolyzer with 6 stages and a treatment and stripping time of 18 minutes the following composition is obtained:

| | |
|---|---|
| NH$_3$ | 0.8% weight |
| CO$_2$ | 0.2% weight |
| urea | <1 ppm weight |
| H$_2$O | 99.0% weight |
| | 100.0% weight |

In the case where a stripping gas is used besides stripping steam the composition to be expected is about:

| | |
|---|---|
| NH$_3$ | 0.3% weight |
| CO$_2$ | 0.1% weight |
| urea | <1 ppm weight |
| H$_2$O | 99.6% weight |
| | 100.0% weight |

Obviously modifications and variations available to the average technician in this field may be introduced in the process and in the equipment described, without however going outside the bounds of the scope and spirit of the invention.

I claim:

1. In a process for the removal of urea, ammonia and carbon dioxide from a dilute process water stream leaving a urea synthesis plant comprising the steps of hydrolyzing the urea and desorbing ammonia and carbon dioxide thus produced, the improvement comprising:

decomposing said urea into ammonia and carbon dioxide while simultaneously stripping ammonia and carbon dioxide thus produced by injecting independent steam streams into at least four consecutive stages;

maintaining each of said stages at a temperature between 150° C. and 262° C. and at a pressure between 15 and 50 bar;

removing from each of said stages a gaseous stream including said ammonia and carbon dioxide;

whereby the residual urea content in the water leaving the last stage is reduced below at least 1 ppm.

2. A process according to claim 1, wherein said urea decomposition and ammonia and carbon dioxide stripping steps are carried out in 4 to 30 consecutive stages.

3. A process according to claim 1 wherein the pH of the dilute process water stream is controlled by injecting metered amounts of carbon dioxide into at least one of said stages.

4. A process according to claim 1, further comprising the step of injecting an independent stream of inert gas, air and/or carbon dioxide into at least one of said stages.

5. In a process for the removal of urea, ammonia and carbon dioxide from a dilute process water stream leaving a urea synthesis plant comprising the steps of hydrolyzing the urea and desorbing ammonia and carbon dioxide thus produced, the improvement comprising:
decomposing said urea into ammonia and carbon dioxide by injecting independent steam streams into at least four consecutive stages;
maintaining each of said stages at a temperature between 150° C. and 262° C. and at a pressure between 15 and 50 bar;
simultaneously stripping ammonia and carbon dioxide thus produced by injecting an independent stream of a stripping gas into each of said stages;
removing from each of said stages a gaseous stream including said ammonia and carbon dioxide;
whereby the residual urea content in the water leaving the last stage is reduced below at least 1 ppm.

6. A process according to claim 5, wherein said stripping gas is selected from the group consisting of inert gases, air and carbon dioxide.

7. A process according to claim 5, wherein the pH of the dilute process water stream is controlled by injecting metered amounts of carbon dioxide into at least one of said stages.

8. A process according to claim 5, wherein said urea decomposition and ammonia and carbon dioxide stripping steps are carried out in 4 to 30 consecutive stages.

9. A process according to claim 8, wherein the pH of the dilute process water stream is controlled by injecting metered amounts of carbon dioxide into at least one of said stages.

* * * * *